United States Patent
Brunner et al.

(10) Patent No.: US 10,561,810 B2
(45) Date of Patent: Feb. 18, 2020

(54) $O_2$-CONTROLLER (75) Inventors: Josef Brunner, Chur (CH); Marc Wysocki, Chevreves (FR); Thomas Laubscher, Rhazuns (CH)

(73) Assignee: HAMILTON MEDICAL AG, Bonaduz (CH)

( * ) Notice: Subject to any disclaimer, the term of this patent is extended or adjusted under 35 U.S.C. 154(b) by 1419 days.

(21) Appl. No.: 12/162,764

(22) PCT Filed: Jan. 30, 2007

(86) PCT No.: PCT/CH2007/000042
§ 371 (c)(1),
(2), (4) Date: Jul. 30, 2008

(87) PCT Pub. No.: WO2007/085110
PCT Pub. Date: Aug. 2, 2007

(65) Prior Publication Data
US 2008/0314385 A1  Dec. 25, 2008

(30) Foreign Application Priority Data
Jan. 30, 2006 (CH) .......................... 146/06

(51) Int. Cl.
A61M 16/10 (2006.01)
A61M 16/00 (2006.01)

(52) U.S. Cl.
CPC ............................... A61M 16/0051 (2013.01)

(58) Field of Classification Search
CPC .............................................. A61M 16/0051

(Continued)

(56) References Cited

U.S. PATENT DOCUMENTS 4,112,938 A   9/1978 Jeretin
4,421,113 A  12/1983 Gedeon et al.
(Continued)

FOREIGN PATENT DOCUMENTS

EP  0504725  9/1992
EP  0753320  1/1997

*Primary Examiner* — Tan-Uyen T Ho
*Assistant Examiner* — Margaret M Luarca
(74) *Attorney, Agent, or Firm* — Prince Lobel Tye LLP (57) ABSTRACT

The invention relates to a device for the regulation of PEEP and $FiO_2$ of a ventilator for achieving an arterial oxygen partial pressure in the blood of a mechanically ventilated patient. At reading which is representative of the success of the oxygen supply, i.e. the oxygen saturation of the blood is measured with the device, and assigned to one of three regions, which are defined by two characteristic lines. A first control loop is designed to optimise PEEP and $FiO_2$ on assigning a reading to a region which demands a change of the settings, or to retaining the settings with an assignment to the normal region between the characteristic lines. This first control loop carries out such an optimisation at predefined temporal intervals on account of the representative reading ($SaO_2^{REP}$) and a predefined necessary supply intensity. The ventilator is subsequently activated accordingly. Therebetween, if necessary only $FiO_2$ is increased or reduced with a second control loop, if between optimisations by way of the first control loop, the current representative value ($SaO_2^{REP}$) falls below a limit value (characteristic line) which is dependent on the supply intensity, which demands an immediate increase of the oxygen supply.

35 Claims, 2 Drawing Sheets (58) Field of Classification Search
USPC .......... 128/204.21, 204.23, 200.24; 600/532, 600/538, 529
See application file for complete search history.

(56) References Cited

U.S. PATENT DOCUMENTS

| | | | |
|---|---|---|---|
| 5,094,235 A * | 3/1992 | Westenskow et al. .. | 128/204.22 |
| 5,103,814 A * | 4/1992 | Maher ..................... | 128/204.18 |
| 5,315,990 A | 5/1994 | Mondry et al. | |
| 5,365,922 A | 11/1994 | Raemer | |
| 5,388,575 A * | 2/1995 | Taube ..................... | 128/204.23 |
| 5,660,170 A * | 8/1997 | Rajan et al. ............ | 128/204.18 |
| 5,692,497 A * | 12/1997 | Schnitzer et al. ....... | 128/204.21 |
| 5,738,090 A * | 4/1998 | Lachmann et al. ...... | 128/204.23 |
| 5,752,509 A * | 5/1998 | Lachmann et al. ...... | 128/204.23 |
| 5,937,854 A * | 8/1999 | Stenzler .................. | 128/204.23 |
| 6,000,396 A | 12/1999 | Melker | |
| 6,116,241 A * | 9/2000 | Huygen et al. .......... | 128/204.23 |
| 6,148,814 A * | 11/2000 | Clemmer et al. ........ | 128/200.24 |
| 6,532,957 B2 | 3/2003 | Berthon-Jones | |
| 6,532,959 B1 | 3/2003 | Berthon-Jones | |
| 6,557,553 B1 * | 5/2003 | Borrello ................... | 128/204.18 |
| 6,564,798 B1 * | 5/2003 | Jalde ........................ | 128/205.24 |
| 6,581,597 B2 | 6/2003 | Sugiura | |
| 6,612,995 B2 * | 9/2003 | Leonhardt et al. ........... | 600/532 |
| 6,951,217 B2 | 10/2005 | Berthon-Jones | |
| 7,077,132 B2 | 7/2006 | Berthon-Jones | |
| 7,520,279 B2 | 4/2009 | Berthon-Jones | |
| 7,802,571 B2 | 9/2010 | Tehrani | |
| 2001/0007256 A1 | 7/2001 | Sugiura | |
| 2002/0193700 A1 * | 12/2002 | Bohm et al. ................... | 600/533 |
| 2003/0111078 A1 | 6/2003 | Habashi | |
| 2003/0227472 A1 * | 12/2003 | Westinskow et al. ........ | 345/700 |
| 2004/0003813 A1 * | 1/2004 | Banner et al. ........... | 128/204.21 |
| 2004/0069304 A1 * | 4/2004 | Jam .......................... | 128/204.18 |
| 2004/0073130 A1 * | 4/2004 | Bohm et al. ................... | 600/547 |
| 2004/0074497 A1 | 4/2004 | Berthon-Jones | |
| 2004/0173212 A1 | 9/2004 | Berthon-Jones | |
| 2004/0206355 A1 | 10/2004 | Berthon-Jones | |
| 2004/0231670 A1 | 11/2004 | Bassin | |
| 2005/0133032 A1 | 6/2005 | Berthon-Jones | |
| 2006/0086357 A1 * | 4/2006 | Soliman ............ | A61M 16/0051 |
| | | | 128/204.22 |
| 2006/0150974 A1 | 7/2006 | Berthon-Jones | |
| 2007/0028921 A1 * | 2/2007 | Banner et al. ........... | 128/204.21 |
| 2007/0089738 A1 * | 4/2007 | Soliman et al. ......... | 128/202.22 |
| 2007/0163590 A1 | 7/2007 | Bassin | |
| 2008/0168989 A1 * | 7/2008 | Cewers .................... | 128/204.21 |
| 2008/0257349 A1 * | 10/2008 | Hedner et al. ........... | 128/204.23 |
| 2008/0314385 A1 | 12/2008 | Brunner | |

* cited by examiner

O$_2$-CONTROLLER

CROSS-REFERENCE TO RELATED APPLICATIONS

This application is a National Stage under 35 U.S.C. § 371 of International Application No. PCT/CH2007/000042, filed Jan. 30, 2007, which claims the benefit of Swiss Patent Application No. 146/06, filed Jan. 30, 2006, the entirety of each of which is incorporated by reference.

The invention relates to a device and to a method for the regulation of a ventilator in accordance with the requirements of the patient, in particular of the end-expiratory pressure (PEEP) and the inspiratory oxygen concentration (FiO$_2$) in the ventilation gas, with the mechanical ventilation of a patient, as well as to a ventilator with such a regulation.

STATE OF THE ART

The mechanical ventilation of a patient has the aim of keeping the CO$_2$-partial-pressure and the O$_2$-partial-pressure in the arterial blood of the patient to a level which is as normal as possible according to the circumstances. With the mechanical ventilation, one may influence the following factors: a) the ventilation volume by way of the ventilation frequency and the ventilation pressure, b) the lung volume taking part in the gas exchange, by way of the end-expiratory pressure (PEEP), c) the supply of oxygen by way of the oxygen concentration in the ventilation gas (FiO$_2$).

The enrichment of the blood with oxygen is influenced on the one hand in a negative manner by way of the so-called shunt, which is the blood which does not take part in the gas exchange, and on the other hand in a positive manner by the oxygen content of the ventilation gas. One may increase the lung volume participating in the gas exchange by way of increasing the PEEP. By way of this, the shunt may be reduced and the arterial oxygen partial pressure may be increased. The lung with each breath may be supplied with more oxygen by way of increasing the FiO$_2$. The arterial oxygen partial pressure in the blood may likewise be increased by way of this.

A method for providing sufficient alveolar ventilation is known from EP-A-0 753 320 there is known. Since it is not sufficient to supply oxygen and remove carbon dioxide, the document teaches the use of preferably only air with a low inspired oxygen concentration and the minimisation of any damage to the cardio-pulmonary system. To achieve this object, a minimal ratio between inspiration time and expiration time is sought and determined. An optimal respiration rate is then sought and determined. Furthermore, the opening and the closing pressure of the lung is then sought and determined by increasing and decreasing the applied pressure and analysing the partial oxygen pressure of the blood and comparing it with threshold values. The document teaches the ventilation above the closing pressure.

A distressed lung may be kept open by way of the suitable choice of the airway pressure above the alveolar closing pressure. U.S. Pat. No. 6,612,995 B2 discloses a method for determining the alveolar opening or closing of a lung ventilated by an artificial ventilator, comprising the steps of: measuring one of the following values: Haemoglobin oxygen saturation, end-tidal CO$_2$-concentration in the expired gas and CO$_2$-output and changing the airway pressure, wherein the airway pressure level at which the alveolar opening or closing occurs is determined from the observation of the resulting course of the measured value, An apparatus for determining the alveolar opening or closing of a lung comprises
  an artificial ventilator,
  a sensor to measure the above-mentioned value, and
  a data processor which, during the change of the airway pressure, determines the airway pressure level at which the alveolar opening and closing occurs, from the resulting course of the measured value.

With a general setting of a PEEP, with which an as large as possible lung volume participates in the gas exchange, one however does not react to the particularities specific to the patient in an optimal manner. For an optimal setting of the parameters influencing the oxygen supply, an increase of the PEEP on the one hand, and an increase of the FiO$_2$ on the other hand are to be weighed up against one another. Both parameters are to be regulated in a patient-specific manner for optimising PEEP and FiO$_2$. Thereby, one should particularly take into account the fact that not so high PEEPs are possible with haemodynamically instable patients than with haemodynamically stable patients.

OBJECT OF THE INVENTION

It is the object of the invention to provide a device and a method, with which the settings of a ventilator are capable of being automatically set in a patient-specific manner.

This object is achieved according to the invention, in that the device for the regulation of settings of a ventilator for achieving an adapted, mechanical ventilation of the patient comprises at least the following:
  at least one sensor, preferably at least two sensors,
  specifically at least one sensor for the continuous measurement or for the measurement in temporal intervals at least of a reading representative of the success of the supply of the O$_2$ supply and/or at least one sensor for the continuous measurement or measurement in temporal intervals of at least one reading representative of the success of the ventilation,
  a programmed computer,
  which is provided with at least one first electronic control loop functioning in a long-term manner, specifically a control loop in order to optimise PEEP and FiO$_2$, and/or a control loop in order to optimise P$_{insp}$ and RR$_{IMV}$, on account of the representative reading and a predefined necessary ventilation intensity, and said computer being programmed in a manner such that the ventilator in each case is activated according to the current optimisation, and
  which is equipped with at least one second electronic control loop functioning in a short-term manner,
  specifically, a control loop, in order between the optimisations by way of the first control loop, if necessary, to increase the FiO$_2$ on account of the current representative value, and/or a control loop in order between the optimisations by way of the first control loop, if necessary, to increase the ventilation on account of the current representative value.

This provision with a control loop functioning in a long-term manner, and a control loop functioning in a short-term manner, for the regulation of the ventilation and/or the O$_2$ supply, on the one hand permits an optimisation which is adapted over the long term to the requirements of the patient. This reduces the risk of a damage to the lungs. However, one ensures that short-term requirements of the patient are taken into account.

In a preferred embodiment, an oxygen sensor for checking the oxygen supply of the patient, in particular the oxygen saturation in the blood of the patient, as well as a $CO_2$ sensor for checking the ventilation, in particular the arterial $CO_2$-partial-pressure of the patient, and all four control loops are present.

It is particularly the object of the invention to suggest a device and a method, with which the PEEP- and $FiO_2$-settings of a ventilator are capable of being regulated in accordance with the patient.

According to the invention, this object is achieved by the independent claims. The dependent claims define advantageous embodiments of the invention.

A device according to the invention for the control of the PEEP- and $FiO_2$-settings of a ventilator, in order to achieve an adapted arterial oxygen-partial pressure in the blood of a patient mechanically ventilated with the ventilator, comprises at least one oxygen sensor, e.g. a pulsoximeter, and a programmed computer. The oxygen sensor serves for the measurement of at least one reading ($SaO_2^{REP}$) which is representative for the success of the oxygen supply. This measurement is effected in a continuous manner in temporal intervals.

The programmed computer is equipped with a first electronic control loop, in order to optimise PEEP and $FiO_2$ on account of the representative reading ($SaO_2^{REP}$) and a predefined necessary supply intensity. It is furthermore programmed in a manner such that it repeats such an optimisation in predefined temporal intervals, and that the ventilator in each case is activated accordingly. It is furthermore equipped with a second electronic control loop, in order between the mentioned optimisations which are carried out with the first control loop, if necessary, to change $FiO_2$ on account of the currents representative value ($SaO_2^{REP}$).

Such a device permits a short-term adaptation of the oxygen supply on the one hand to the requirements of the patient, and a long-term optimisation of $FiO_2$ and PEEP on the other hand. The optimisation of $FiO_2$ and PEEP requires longer intervals, in order to be carried out efficiently, and reduces the risk of a damage to the lung. The adaptation of $FiO_2$ by the second control loop ensures that such a relatively long interval may not lead to an undersupply of the patient with oxygen.

With the optimisations, either only PEEP or only $FiO_2$ may be adapted. Usefully then, the length of the interval is dependent on which of these parameters was adapted with a preceding optimisation. Advantageously however, in each case an optimised PEEP as well as an optimised $FiO_2$ is computed and simultaneously set.

In order to fulfil its task of the optimisation of PEEP and $FiO_2$, the first control loop usefully contains two algorithms. The first of these two algorithms serves for the computation of a necessary supply intensity. It computes such a value on account of the current representative reading ($SaO_2^{REP}$) and the current supply intensity. The second algorithm serves for determining the individual values for PEEP and $FiO_2$. These are then computed on account of the necessary supply intensity. A function (including the value) of PEEP, a function (including the value) of $FiO_2$, or a function of PEEP and $FiO_2$ may be taken as the supply intensity.

A computation of the individual values for PEEP and $FiO_2$ on account of the supply intensity advantageously results in different results depending on the requirements that a patient brings along. For this reason, a device should have input possibilities for the lung condition, a strategic goal of the ventilation, the haemodynamic stability and possible the age of the patient. The results on computation of the setting values are also influenced by these inputs.

In any case, the setting must ensure an $O_2$-supply. With the device therefore, the first control loop, in particular the first algorithm assigns, assigns the representative reading in each case to one of three regions. These are the regions: "too high a reading", "normal reading", "too low a reading". These regions are defined by at least two characteristic line pairs stored in a memory. Advantageously, two characteristic line pairs are stored for different strategies. Each characteristic line pair has a first characteristic line which assigns in each case different minimal representative values to different quantified supply intensities. This characteristic line therefore forms the border line between the normal region and the region which is too low. The characteristic line pair of course also has a second characteristic line, which assigns in each case different maximal representative values to different quantified supply intensities. This second characteristic line is therefore the border line between the normal region and the region for readings which are too high. Both characteristic lines are distanced to one another and between them, define the normal region for the representative value. Two characteristic lines are present for the first control loop. Two characteristic lines may likewise be present with the second control loop. The characteristic lines of the first control loop are then arranged at a first, smaller distance to one another, with the second control loop however at a second larger distance to one another. The second control loop may only have one lower characteristic line. This means that with the second control loop, the upper characteristic line lies at 100% $FiO_2$, and therefore may not be exceeded. The normal region which is applicable to the first control loop, in any case falls completely in the larger normal region which is applicable to the second control loop. If the representative reading falls in this normal region, then the settings of the ventilator which concern the supply with oxygen, are retained. If the reading falls into the normal region of the first control loop, then it compellingly also falls in the normal region of the second control loop. Since the normal region of the second control loop is wider than that of the first control loop, the second control loop may only become effective when, between the adaptations of the settings by way of the first control loop, the reading moves so far out of the normal region of the first control loop, that it also goes out of the normal region of the second control loop. The second control loop therefore reacts in a more tolerant manner, but in a shorter interval than the first control loop.

If thanks to the increase of $FiO_2$ by way of the second control loop, the reading lies within the normal region of the second control loop, then it may despite this lie outside the tighter normal region of the first control loop. The first control loop the next time will therefore again have to carry out the optimisation afresh, and, if the condition of the patient permits this, increase PEEP in many cases, in order to achieve an optimisation of PEEP and $FiO_2$. Thereby, the first control loop may base its computation on the supply intensity resulting after the correction by the second control loop. Advantageously however, such a change by the second control loop is not taken into account, but the computation is based on the intensity which results from the settings set by the first control loop.

The three regions are advantageously defined depending on a strategic goal. Different characteristic line pairs are therefore stored in the memory. Different characteristic line pairs represent a forced withdrawal or a normal ventilation with a tendential withdrawal. Therefore a strategic goal may advantageously be selected with the device. The first algorithm then falls back on a different characteristic line pair corresponding to the strategic goal, depending on the selected strategic goal. Depending on whether the current reading with the applied characteristic line pair, still lies within the normal region or not, accordingly at least one of the two parameters PEEP and $FiO_2$, or both simultaneously, are changed, and thus also the intensity is changed. The characteristic lines lie differently with another characteristic line pair, so that the change of the two parameters does not happen in the same situation. A strategic goal may be followed up by way of this.

The device further usefully has an input possibility for a patient parameter characterising the lung condition of the patient. The patient parameter is then taken into account in the second algorithm of the first control loop. A change of the parameter may therefore influence the individual values for the supply parameters.

Usefully, in a similar manner, an input possibility for a haemodynamic input value is provided, which characterises the haemodynamic stability of the patient. This haemodynamic input value is taken into account in the second algorithm, in order with the optimisation of $FiO_2$ and PEEP to ensure that the selected end-expiratory pressure does not burden the haemodynamics too much. The haemodynamic input value may be inputted manually, or however may be evaluated automatically on account of a blood pressure monitoring, or a monitoring of another value indicating the haemodynamics. An automatic switch-over to a mode for haemodynamically instable patients is effected on account of this value, for example on account of the average blood pressure (e.g. the patient is classed as being haemodynamically stable at a blood pressure for example of more than 65 mmHg).

If this value indicating the haemodynamics is so bad, that one is to assume haemodynamics which may not be burdened any further, e.g. thus with an average blood pressure of 65 mmHg or lower, then a controller is automatically switched on, which ensures that the oxygen concentration $FiO_2$ is increased instead of a PEEP increase. This controller furthermore checks as to whether a value indicating the haemodynamics is present, which permits this decision. In the case that no value indicating the haemodynamics is present, the controller increases PEEP in only two cases, specifically when the current PEEP does not lie above 5 $cmH_2O$, and when a good circulation is present, which is ascertained with the pulsoximeter, and PEEP lies maximally at 10 $cmH_2O$. If these conditions are not fulfilled, and there is no new value indicating the haemodynamics as a basis, the controller gives the apparatus user the decision as to whether PEEP or $FiO_2$ is to be increased.

With the optimisation of PEEP and $FiO_2$ with the first control loop, usefully one applies functions, with which the lung condition and the haemodynamics of the patient may be taken into account. Therefore different, diagrammatically representable functions are deposited in a memory at the device. These functions in each case allocate a value for PEEP to a value for $FiO_2$. The second algorithm on account of one of these functions, determines the current values for PEEP and $FiO_2$, or whether $FiO_2$ and/or PEEP must be increased or reduced.

The second algorithm selects the fitting function according to the inputted input values. One function which is applied with instable haemodynamics, advantageously assigns $FiO_2$ and PEEP to one another, irrespective of whether the supply intensity is increased or reduced. One function which on the other hand is applied with stable haemodynamics, forms a loop and therefore assigns $FiO_2$ and PEEP to one another depending on whether the supply intensity is increased or reduced. Tendentially, with a reaction of the necessary intensity, firstly $FiO_2$ is reduced, but with a necessary increase of the intensity however, tendentially firstly PEEP is increased, or PEEP and $FiO_2$ are increased alternately or simultaneously.

Advantageously, the computer is programmed such that a so-called recruitment manoeuvre is carried out before increasing the PEEP, in order after the recruitment manoeuvre to artificially respirate with the increased PEEP. Such a recruitment manoeuvre may be carried out for example by way of ventilating in the CPAP-mode for 30 seconds with 40 $cmH_2O$ and without pressure support. Lung parts which are not ventilated are to be opened by way of this, which are then to be kept open with the increased PEEP.

Since such a device regularly controls the ventilations via the ventilation rate and the ventilation pressure, as well as the oxygen supply via $FiO_2$ and PEEP, the invention may also be described as follows. The device for the regulation of the settings of a ventilator has sensors for monitoring the success of the ventilation and of the oxygen supply. It further comprises a programmed computer for activating the ventilator with the purpose of the regulation of the ventilation and of the oxygen supply on account of the sensor signals. Four control loops are programmed in the computer, specifically:

1. A first ventilation control loop, in order to set the target frequency and the inspiration pressure in accordance with the patient. A target value for the intensity of the ventilation and a target value for the arterial $CO_2$-partial-pressure of the patient and corresponding to present intensity of the ventilation are kept within limits with these settings. The first ventilation control loop effects a long-term regulation of the ventilation settings.

2. A second ventilation control loop, in order, in a temporally limited manner, to reduce the target value for the arterial $CO_2$-partial-pressure and to increase the target value for the ventilation intensity. This however is only to be effected when the total respiratory frequency exceeds the computed target frequency (for a certain time duration) by a certain value. This second ventilation control loop effects a short-term correction of the ventilation settings for relieving the patient who demands a lower $CO_2$-partial-pressure by way of his own increased activity.

3. A first $O_2$-supply control loop in order to set the oxygen concentration of the ventilation gas, and the end-expiratory pressure, and thus to achieve a target value for the oxygen supply of the patient. This first $O_2$-supply control loop effects a long-term optimisation of PEEP and $FiO_2$.

4. A second $O_2$-supply control loop, in order merely to increase the oxygen concentration in the ventilation gas between two optimisations by way of the supply control loop, as soon as a representative reading for the success of the oxygen supply falls below a limit value. This second $O_2$-supply control loop effects a short-term securing of an adequate oxygen supply.

Such a device is preferably a constituent of a ventilator. Advantageously, the ventilator has a sensor for checking the success of the oxygen supply, a sensor for the control of the haemodynamic stability of the patient, and a computer with input possibilities for the haemodynamic stability of the patient, for the input of a patient parameter, as well as a strategic goal. Advantageously, the haemodynamics and the oxygen supply is monitored with the same sensor. The computer is programmed in order to automatically compute PEEP and $FiO_2$ on account of the sensor values and the input values and to regulate the settings of the ventilator accordingly.

The method according to the invention for the regulation of PEEP and $FiO_2$ of a ventilator serves for achieving an arterial oxygen partial pressure in the blood of a patient being mechanically ventilated. It operates with two control loops: With a first control loop, in the span of a first interval, the values of PEEP and $FiO_2$ are optimised and the ventilator is activated accordingly. After a change, the interval is e.g. 90 sec to 3 min, until a new operation is computed. The interval is advantageously shorter (90 sec) with an increase of the supply, than with a reduction of the supply intensity (180 see). This first control loop, for this, is based on a value ($SaO_2^{REP}$) which is representative of the oxygen content (saturation) of the arterial blood, and a necessary predefined supply intensity. If necessary, $FiO_2$ is increased in the span of a second, shorter interval (e.g. 15 seconds) with a second control loop. The second control loop thereby is based on the representative value ($SaO_2^{REP}$). $FiO_2$ is brought very rapidly, as the case may be, to 100%, by way of the second control loop. Advantageously, straight away, one enriches with 100% oxygen with an increase of the oxygen content in the ventilation air. On reducing the oxygen content, because the saturation has become sufficient after the increase, this increase is again reduced to 90% within a short time (3 minutes).

The representative value is usefully a continuously measured reading which e.g. is representative of the oxygen saturation of the blood. Even if invasive methods were also to be possible, non-invasive measurement methods are preferred, so that the representative value is preferably acquired with a pulsoximeter. The representative value may be deduced from a measurement with a single sensor. It may however also be summarised from different readings of several sensors, which increases the reliability of the reading.

The representative value may also be computed from a $CO_2$-balance of the respiratory gases, if one may apply a blood gas measurement.

The first control loop is advantageously divided up into two algorithms. A necessary supply intensity (function of PEEP) is computed with a first algorithm on account of the representative value and of the current supply intensity. The individual values for PEEP and $FiO_2$ are evaluated with a second algorithm on account of the necessary supply intensity. Usefully, a patient parameter which characterises the lung condition is characterised in a second algorithm.

The first algorithm of the first control loop assigns the representative value advantageously in each case to one of three regions. A correction of the setting therefore needs only to be effected when the representative value lies outside a normal region. The second control loop assigns the representative reading to one of two regions. It initiates a correction of the $FiO_2$-setting, in the case that the reading is so low that it no longer falls in the normal region, and therefore displays an insufficient oxygen supply. These regions are defined in the first control loop by two characteristic lines which are distanced to one another, and which in each case assign a supply intensity to a minimal and maximal representative value. Between them, they define a normal region for the representative value. Only a lower characteristic line is fixed in the lower control loop, and this line defines that the second control loop is activated when the reading falls below this characteristic line. The lower characteristic line for the minimal representative value, with the second control loop, lies lower than with the characteristic line pair used in the first control loop. Analogously, the upper characteristic line for the maximal representative value, in the first control loop, lies below the maximal reading of 100% of the second control loop.

Usefully a haemodynamics input value which characterises the haemodynamic stability of the patient is taken into account in the second algorithm of the first control loop. With instable haemodynamics, the maximal end-expiratory pressure PEEP is limited to such a depth, that practically only the oxygen concentration of the ventilation air continues to be adapted.

The second algorithm determines the current values for PEEP and $FiO_2$ advantageously on account of a diagrammatically representable function. The function in each case allocates a value for PEEP to a value for $FiO_2$.

The second algorithm uses different functions, depending on what current haemodynamic input value, and what current patient parameter is present, in order to fix the values of $FiO_2$ and PEEP.

With instable haemodynamics, the function assigns $FiO_2$ and PEEP to one another, independently of whether the supply intensity is increased or reduced.

With stable haemodynamics on the other hand, the function forms a loop. For this reason, $FiO_2$ and PEEP are assigned to one another depending on whether the supply intensity is increased or reduced.

These diagrammatically representable functions are advantageously configurable according to wishes. They may therefore be configured and modified according to new information or according to personal convictions of physicians. For this, one may for example determine 10 points, between which the diagrammatically represented function runs in a straight line. These points may be displayed and set in an infinite manner or within limits.

An adaptation of PEEP and $FiO_2$ is effected after each time interval of $\Delta t$, as long as the readings lie below the normal region. Thereby, for example PEEP is increased by 2 $cmH_2O$ (a recruitment manoeuvre is carried out for this) and $FiO_2$ is fixed by way of the currently applicable function. If the haemodynamics are capable of being monitored during the recruitment manoeuvre, then the recruitment manoeuvre may be terminated as soon as signs for instable haemodynamics are observed.

With a reduction of the intensity, accordingly PEEP is reduced by 2 $cmH_2O$ and $FiO_2$ is adapted according to the valid function. This is repeated until the reading $SaO_2$ lies within the normal region.

The second algorithm, with a necessary intensification of the supply, usefully on account of an assessment of the blood pressure or of another reading which provides information on the haemodynamics of the patient, decides as to whether PEEP may be increased to the required extent and whether only $FiO_2$ may be increased.

Advantageously, different characteristic line courses form the basis of the second control loop depending on a patient parameter. This permits the characteristic lines and therefore the normal region to be adapted to the requirements specific to the patient or specific to the disease, but above all to the strategic goals.

Furthermore, the present invention may be defined as a method for the automatic regulation of the settings of a ventilator, with which method the following steps are carried out: with a first ventilation control loop, the target frequency and the inspiration pressure are set, in order to fulfil target values for an arterial $CO_2$-partial-pressure in the patient blood and for a ventilation intensity, in accordance with the patient.

By way of a second ventilation control loop, for a limited time, the target value for the arterial $CO_2$-partial-pressure is reduced, and the target value for the ventilation intensity is increased. This however only occurs when the total respiratory frequency exceeds the computed target frequency by a certain value. With a first $O_2$-supply control loop, the oxygen concentration of the ventilation gas, and the end-expiratory pressure are set, in order to fulfil target values for the supply intensity and an oxygen concentration in the patient blood, in accordance with the patient.

And finally, the oxygen concentration in the ventilation gas is increased by way of a second supply control loop. This increase only occurs when a representative reading ($SaO_2^{REP}$) for the oxygen concentration between two settings by way of the supply control loop in the patient blood falls below a certain lower limit value, said limit value lying below the normal region of the first control loop.

The invention also relates to a ventilator with a control which is designed in order to carry out one of the above described methods.

Such a ventilator is provided with a sensor for measuring a reading which is representative of the oxygen partial pressure, a sensor for the monitoring of the haemodynamic stability, a programmable control with input possibilities for haemodynamic stability of the patient, for the input of a patient parameter, and for the automatic computation and activation of a PEEP and a $FiO_2$ whilst taking these input values into account.

The invention is hereinafter explained in detail by way of examples and the Figures.

Figure 5:
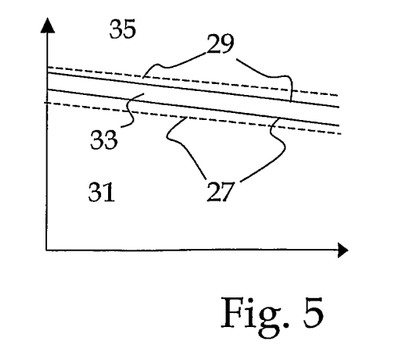
FIG. 5 shows characteristic lines for the assessment of a representative value for the arterial oxygen partial pressure in the blood of the patient. x-axis supply intensity, y-axis representative value $SaO_2^{REP}$

The diagram represented in FIG. 5 schematically shows a circuit with which the method according to the invention may be used with the supply of a patient 11 with oxygen.

Figure 1:
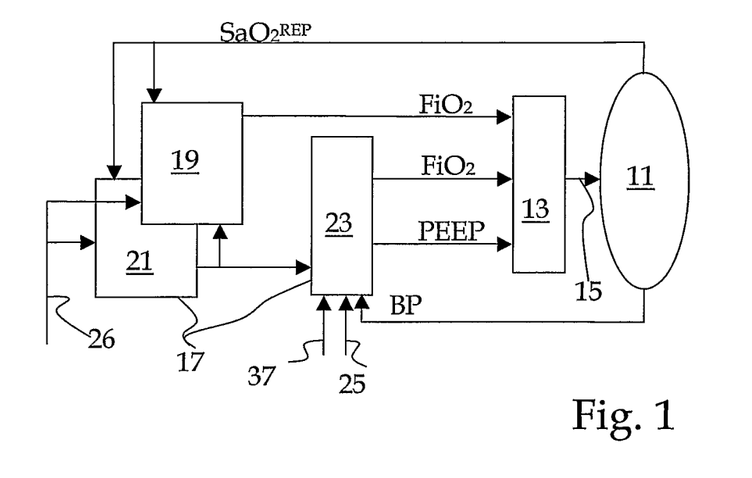
FIG. 1 schematically shows the regulation of the oxygen supply of a patient with a ventilator.

The oxygen is supplied to the patient 11 by way of a pressure source (ventilator) 13 with the ventilation air 15. The pressure source 13 is controlled by a circuit. The circuit consists of a first control loop 17 and of a second control loop 19, which both ensure an adequate oxygen supply. The first control loop comprises two algorithms, specifically a first algorithm 21 which defines the necessary supply intensity, and a second one 23 which evaluates the suitable setting with regard to $FiO_2$ and PEEP and activates the ventilator 13 accordingly.

The product of FiO2(%) and PEEP (cmH$_2$O) may be defined as the supply intensity. The supply intensity then with a PEEP below 1 is always 1*$FiO_2$. With a supply intensity which is defined as a linear function of $FiO_2$ and PEEP, however a change of PEEP is weighted too little in comparison to a change of $FiO_2$. It is therefore useful, in order to better reflect the intensity of the ventilation in this value, to increases the weighting of PEEP, or in a simplifying manner, to even not take $FiO_2$ into account at all with a definition of the supply intensity. In the latter case, the supply intensity is a function of PEEP alone. This necessary supply intensity, also called "treatment level", is fixed for the patient 11 in the first algorithm 21 of the first control loop 17. The basis for this fixing is an input of a patient parameter 25. The following circumstances are differentiated with the patient parameters:

normal patients,
COPD-patients with an increased lung resistance compared to normal patients
ARDS-patients with an increased lung stiffness compared to normal patients,
patients with haemodynamic instability,
patients with brain injury.

Furthermore, a strategic differentiation is made between normal operation (with tendential withdrawal) and forced withdrawal. The input of this strategic goal is indicated with the reference numeral 26.

One uses different characteristic lines 27, 29 with an assessment of the arterial oxygen partial pressure, depending on the strategy. These characteristic lines 27, 29 are represented by way of example in FIG. 5. The supply intensity increases from the left to the right on the X-axis, and the Y-axis contains the values for the representative value for the oxygen partial pressure in the blood, increasing to the top. Several characteristic line pairs are present, which in each case assign a minimal and a maximal value of the representative value to a supply intensity. The characteristic line pairs are differentiated from one another in the drawing by way of different line qualities. The characteristic lines shown in an unbroken manner apply to the first control loop, the interrupted characteristic lines apply to the second control loop.

The characteristic line pairs run differently, depending on which strategic goal is followed, and whether they apply to the first or second control loop. With a strategy for the forced withdrawal, the applicable normal region has lower values for the arterial oxygen saturation than the normal region, which is applicable with a strategy for normal ventilation.

On this basis, a representative value, in the represented embodiment example, a representative reading for the saturation of the blood $SaO_2^{REP}$ measured with a pulsoximeter, is classed into one of the three regions 31, 33, 35 defined by the characteristic lines. The reading is therefore graded either as normal when it falls in the region 33, as too high when it falls in the region 35, or as too low when it falls in the region 31.

If a current representative value falls between the characteristic lines of the currently applicable characteristic line pair, then it is considered as normal and the ventilation is continued in an unchanged manner. If the current value however falls below the lower characteristic line 27 or above the upper characteristic line 29, then the supply intensity is increased or reduced respectively.

Figure 2:
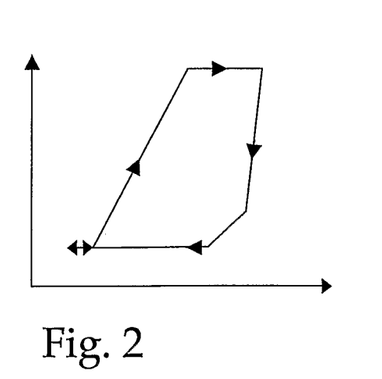
FIG. 2 shows a diagrammatically represented function curve for adapting $FiO_2$ and PEEP with an increase or reduction of the necessary supply intensity for normal patients. x-axis PEEP, y-axis $FiO_2$
Figure 3:
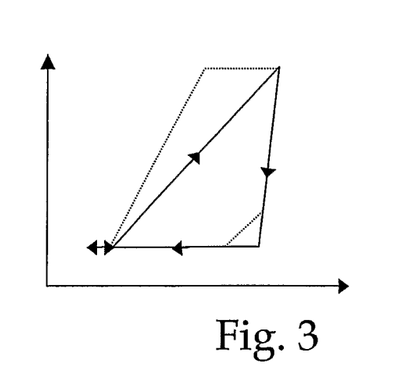
FIG. 3 shows a diagrammatically represented function curve for adapting $FiO_2$ and PEEP with an increase or reduction of the necessary supply intensity for patients with a stiff lung and/or with a high ventilation resistance in comparison to the function of the normal patients x-axis PEEP, y-axis $FiO_2$

The new values for the supply intensity together with an input value 37 for the haemodynamic stability of the patient, forms the basis for the measurement of PEEP and $FiO_2$. It is decided by way of functions which are schematically represented in the FIGS. 2 to 4 as to whether PEEP or $FiO_2$ are to be increased or reduced. With normal patients, the PEEP is firstly increased with an increasing supply intensity. Later either PEEP or FiO$_2$ or both together are increased. PEEP is never lifted above the limit value defined by the curve. From a certain supply intensity, PEEP as well as FiO$_2$ are increased, until one ventilates with pure oxygen. Thereafter, it is only the end-expiratory pressure PEEP which is still increased. Tendentially however, firstly the oxygen component in the ventilation air is reduced. The oxygen component is reduced until the returning curve of the function is intersected. This curve runs from the most extreme corner with the highest supply intensity steeply back to a supply with a low oxygen component in the ventilation gas. Up to this, the PEEP is only slightly reduced. From this point, the ventilation pressure and the oxygen content are reduced symmetrically. Finally, one ventilates with an oxygen content of 30%, and for this reason only PEEP can still be reduced.

With the function for COPD- and ARDS-patients (FIG. 3), one increases from the same supply level of PEEP and FiO$_2$ in a proportional manner up to their extreme values. With the reduction of the supply intensity, the curve firstly runs identically to the curve for normal patients. For this reason, it is chiefly the oxygen content which is reduced, and the PEEP is only slightly reduced. The curve retains this direction until an FiO$_2$ of 30%. After this, solely PEEP is reduced.

If under certain circumstances, an automatic evaluation of PEEP and FiO$_2$ may not be based on readings and programmed in a secure manner, which may be the case e.g. for PEEP in the case of a COPD patient, the device is programmed in a manner such that the respective value must be inputted in a manual manner.

Figure 4:
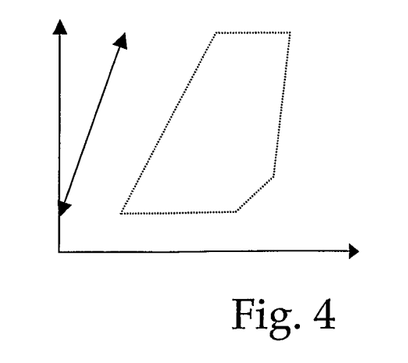
FIG. 4 shows a diagrammatically represented function curve for adapting $FiO_2$ and PEEP with an increase or reduction of the necessary supply intensity for haemodynamically instable patients, in comparison to the function for normal patients. x-axis PEEP, y-axis $FiO_2$

With patients with instable haemodynamics, PEEP is only changed according to FIG. 4 in a region of 0 to 5 mbar. In this region however, the oxygen content of the ventilation gas is greatly increased with an increase in the supply intensity. On taking down the supply intensity, the second algorithm follows the same curve as with the intensification. Since an increased PEEP represents a burden to the heart, one mainly reacts with FiO$_2$ with haemodynamically instable patients.

Figure 6:
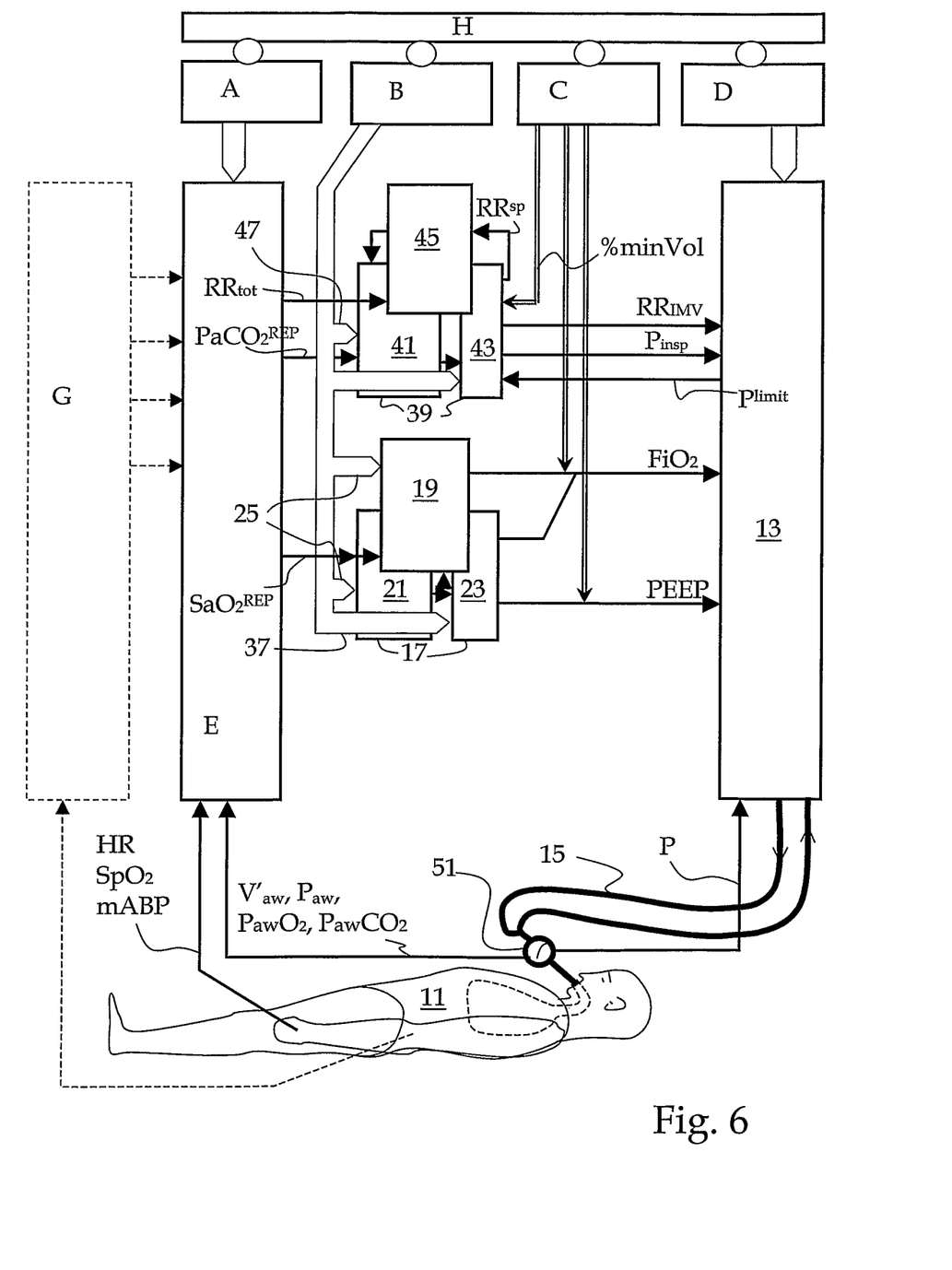
FIG. 6 shows a schematic representation of a ventilator with control loops for the ventilation and the oxygen supply.

A ventilator is represented diagrammatically in FIG. 6. This Figure also contains the diagram represented in FIG. 1. The first O$_2$-supply control loop 17 has both algorithms 21 and 23 which in a longer interval weigh up FiO$_2$ and PEEP against one another and optimise these over the longer term. A second supply control loop 19, if required, in the meanwhile increases the FiO$_2$, in order in the short term to ensure the oxygen supply of the patient.

Apart from this, a regulation is present in order to ensure the ventilation of the patient. This regulation has a first ventilation control loop 39 with the algorithms 41 and 43. The first algorithm 41 computes a new ventilation intensity on account of a present ventilation intensity and a current representative reading PaCO$_2^{REP}$ for the arterial CO$_2$-partial-pressure of the patient. This newly evaluated value forms the basis of the second algorithm. On this basis, it computes a target frequency RR$^{SP}$, machine frequency RR$_{IMV}$, and an inspiration pressure P$_{insp}$. The target frequency is compared to the current, total respiratory frequency in a second ventilation control loop 45. If the patient breathes actively by a certain amount more frequently that corresponds to the target frequency, then the ventilation intensity is increased by way of the second ventilation loop 45, and the target value for PaCO$_2^{REP}$ is reduced. This measure is based on the assumption, that the patient desires a lower CO$_2$-partial-pressure and thus increases the frequency. As soon as the total respiratory frequency RR$_{tot}$ and the target frequency RR$^{SP}$ correspond to one another over a certain time, e.g. 10 minutes, an intensification of the ventilation initiated by the second ventilation control loop 45 is cancelled again.

The ventilation of the patient is carried out by the mechanical ventilation unit 13 according to the values for the inspirational pressure and the ventilation rate which have been deduced with the first and the second ventilation control loop. The oxygen supply is carried out by the mechanical ventilation unit 13 according to the values FiO$_2$ for the oxygen content of the respiratory gas and PEEP for the remaining end-expiratory pressure. The patient 11 therefore obtains the predefined ventilation. The pressures on breathing in and out are measured at the proximal flow sensor 51. Different parameters which are monitored by the apparatus are computed therefrom.

Furthermore, a block E is represented, which indicates an interface, with which those monitoring values which form the basis of the ventilation and the oxygen supply, are controlled (e.g. plausibility check) and are processed into bases for the control loops 39 and 17.

Block G indicates that the monitoring values SpO$_2$, pulse, PaCO$_2$, tcpCO$_2$, mABP etc. may also come from an external monitoring apparatus G, and does not necessarily need to be fed directly from a sensor into the block E.

Furthermore, the blocks A, B, C, D and a block H connecting these is represented. The blocks A to D indicate the manual input possibility of certain settings.

A: Manual input of blood pressure and blood gas values.
B: Input of ventilation strategies, disease parameters, size and sex of the patient, said values forming a basis on evaluation of the specific values for the oxygen supply and the ventilation.
C: Adaptation or manual setting of all setting values.
D: Manual setting of alarm limits, pure oxygen ventilation, or carrying out manoeuvres such as suctioning, etc.

Block H indicates the user interface with a screen display, via which interface all these input possibilities are capable of being used, and on which the set values and the measured values are represented.

The interface according to block E processes a representative value from a series of readings and indexes these with an index for its reliability. For this reason, the oxygen saturation of the blood may for example be measured simultaneously with two independent sensors, e.g. two pulsoximeters, a pulsoximeter and breathing gas sensors, etc. The readings SpO$_2$ and PawO$_2$ and PawCO$_2$ provided by the sensors are then (e.g. whilst taking a blood gas measurement into account) summarised into the representative value SaO$_2^{REP}$.

The same also applies to PaCO$_2$. The value of the end-tidal CO$_2$-measurement is taken as a representative value PaCO$_2^{REP}$.

The average arterial blood pressure mABP is either evaluated from invasive measurements or non-invasive measurements of the blood pressure. Other readings which provide information on the haemodynamics (e.g. perfusion index) may be deduced from the measurement results of the pulsoximeter.

The device regulates the settings of the ventilation parameters of respiratory pressure, P$_{insp}$, respiratory rate RRIMV, inspiration time TI, oxygen concentration in the respiratory gas FiO$_2$, and the end-expiratory pressure PEEP in a manner such that the representative readings PaCO$_2^{REP}$ and SaO$_2^{REP}$ fall in a normal region. If a reading falls in the normal region, then the setting mostly remains unchanged. A change is only carried out when the spontaneous rate lies above the computed target rate by a certain amount. If the representative reading does not fall in the normal range which is defined depending on the supply intensity or depending on the intensity of the ventilation, the ventilation parameters are changed. With a change, patient parameters such as lung condition (compliance, resistance, COPD, ARDS), haemodynamic stability, brain injury, patient activity, age etc. are taken into account, e.g. by way of corresponding functions or the selection of normal regions. With an oxygen supply which is too low, the PEEP may be increased as the case may be. A recruitment manoeuvre is carried out with an increase of the end-expiratory pressure, in order thereafter to artificial respirate with the increased PEEP. A PEEP-increase however is only carried out to a low extent with haemodynamically instable patients, and thereby, such a recruitment manoeuvre may be done away with.

Concluding, the invention relates to a device for the control of PEEP and $FiO_2$ of a ventilator for achieving an arterial oxygen partial pressure in the blood of a mechanically artificial respirated patient. At least one reading which is representative of the success of the oxygen supply, i.e. the oxygen saturation of the blood, is measured with the device in a continuous manner or at intervals, and assigned to one of three regions, which are defined by two characteristic lines. Two of the three regions demand a reduction or an increase of the supply by way of an adaptation of the settings, a third, specifically a normal region between the characteristic lines, permits the retention of the given settings. A first control loop is designed to optimise PEEP and $FiO_2$ on assigning a reading to a region which demands a change of the settings, or retain the settings with an assignment to the normal region. This first control loop carries out such an optimisation at predefined, temporal intervals on account of the representative reading ($SaO_2^{REP}$) and a predefined necessary supply intensity. The ventilator is subsequently activated accordingly. Within these temporal intervals, i.e. between two optimisations of the first control loop, if necessary, only $FiO_2$ is increased with a second control loop, if between optimisations by way of the first control loop, the current representative value ($SaO_2^{REP}$) falls below a limit value (characteristic line) which is dependent on the supply intensity and which demands an immediate increase of the oxygen supply, and reduced with the second control loop, if the current representative value ($SaO_2^{REP}$) is above said limit value again.

The invention claimed is:

1. A device for regulating PEEP- and $FiO_2$-settings of a ventilator for achieving an adapted, arterial oxygen level in blood of a patient mechanically ventilated with the ventilator, the device comprising:
   a sensor configured for delivering at least one representative reading that is representative of an oxygen supply derived from a continuous measurement or from a measurement in temporal intervals, and
   a programmed computer configured to determine values for PEEP and $FiO_2$, wherein the programmed computer comprises:
   a first electronic control loop to control optimizations for values for PEEP and $FiO_2$ having a first algorithm to compute a necessary supply intensity based on the at least one current representative reading and a current supply intensity, and a second algorithm to evaluate the individual values for the PEEP and the $FiO_2$ based on a necessary supply intensity, the first electronic control loop being repeated in temporal intervals having a first duration and the ventilator in each temporal interval activated accordingly, and
   a second electronic control loop operating between the optimizations controlled by the first electronic control loop to increase the $FiO_2$ based on a current representative reading alone, the second electronic control loop being repeated in temporal intervals having a second duration shorter than the first duration;
   wherein the first electronic control loop in each temporal interval assigns a representative reading to one of three regions which are defined by a characteristic line pair, each characteristic line of the characteristic line pair being defined by oxygen supply intensity on one axis and a representative value of oxygen partial pressure in blood on another axis, and only carries out a change of the parameters FiO2 and/or PEEP when a reading lies outside a middle normal region, wherein the characteristic line pair has a first characteristic line which assigns different minimal representative values of oxygen partial pressure in blood to different values of oxygen supply intensity, and a second characteristic line which assigns different maximal representative values of oxygen partial pressure in blood to different values of oxygen supply intensity, said first and second characteristic lines being distanced from one another and between them defining the middle normal region for a representative value, and
   the second electronic control loop assigns the representative reading in each temporal interval to one of two regions which are defined by a single characteristic line, and only carries out a change of the FiO2 when the reading lies below the single characteristic line, wherein the single characteristic line assigns different maximal representative values of oxygen partial pressure in blood to different values of oxygen supply intensity, and wherein the single characteristic line used in the second electronic control loop lies below the first characteristic line of the characteristic line pair used in the first electronic control loop, and the middle normal region which is used with the first electronic control loop falls completely within a normal region present above the single characteristic line with the second electronic control loop.

2. The device according to claim 1 wherein the necessary supply intensity computed by the first algorithm is a function of the PEEP.

3. The device according to claim 1 wherein the necessary supply intensity computed by the first algorithm is a function of $FiO_2$.

4. The device according to claim 1, wherein the oxygen supply is measured by a pulsoximeter.

5. The device according to claim 1, wherein:
   an input for a patient parameter, which characterizes a lung condition of the patient, is taken into account in the second algorithm, and
   a change of the patient parameter leads to a different optimization of the PEEP and the $FiO_2$.

6. The device according to claim 1, wherein the first interval is between 90 and 180 seconds and the second interval is approximately 15 seconds.

7. The device according to claim 1, wherein a plurality of different characteristic line pairs for the first electronic control loop and of different characteristic single lines for the second electronic control loop are stored in a memory and are selectable, each different characteristic line pair and different characteristic single line corresponding to one of a plurality of strategic goals.

8. The device according to claim 7, wherein a strategic goal is selectable, and the computer, depending on the selected strategic goal, selects the characteristic line pair and single line to be used in the first and second control loops respectively, from memory, corresponding to the strategic goal.

9. The device according to claim 1, wherein a controller is present, which on account of a current PEEP and at least one value indicating haemodynamics of the patient, the at least one value including a blood pressure or a reading which is a measure of a peripheral circulation, decides whether a PEEP increase demanded by the first electronic control loop is carried out, or the $FiO_2$ is increased instead of a suggested PEEP-increase, or a decision is left to a user of the device.

10. The device according to claim 1, wherein an input possibility for a haemodynamic input value which characterizes a haemodynamic stability of the patient, that includes a haemodynamics input value that is used in the second algorithm on optimizing $FiO_2$ and PEEP.

11. The device according to claim 10, wherein the second algorithm includes a function which is applied with unstable haemodynamics, said function assigning the $FiO_2$ and the PEEP to one another independently of whether a supply intensity is increased or reduced.

12. The device according to claim 1, wherein different functions, represented diagrammatically, are stored in a memory and assign a value for the PEEP to a value for the $FiO_2$, and the second algorithm determines current values for the PEEP and the $FiO_2$ on account of one of the different functions.

13. The device according to claim 12, wherein an input of the second algorithm includes an input representing a haemodynamic status of the patient, and an input representing the current patient parameter.

14. The device according to claim 13, wherein the second algorithm includes a function which is applied with stable haemodynamics, said function forming a loop and assigning $FiO_2$ and PEEP to one another, depending on whether a supply intensity is increased or reduced.

15. The device according to claim 12, wherein the different functions are programmed in a manner configurable by a human operator.

16. The device according to claim 1, wherein the computer is programmed such that a recruitment maneuver is carried out before an increase of the PEEP.

17. A device for regulating settings of a ventilator, with sensors for monitoring a success of a ventilation and an oxygen supply, with a programmable computer for activating the ventilator for controlling the ventilation and the oxygen supply on account of sensor signals, comprising:
a first ventilation control loop programmed in order to set a target frequency and an inspiration pressure in accordance with a patient, and thus achieve a target value for an intensity of a ventilation, and a target value for an arterial $CO_2$-partial pressure of the patient which corresponds to a present intensity of the ventilation,
a second ventilation control loop programmed for analyzing whether a total respiratory frequency exceeds a computed target frequency by a certain value, and when the total respiratory frequency exceeds the computed target frequency by the certain value, to reduce the target value for the arterial $CO_2$-partial pressure and to increase the target value for the ventilation intensity, in a temporally limited manner based on the analyzing,
a first supply control loop to control optimizations for values for PEEP and $FiO_2$ programmed with a first algorithm to compute a necessary supply intensity based on at least one representative reading and a current supply intensity, and a second algorithm to evaluate individual values for end expiratory pressure (PEEP) and ventilation gas ($FiO_2$) on account of a necessary supply intensity and further programmed, in order to set an oxygen concentration of $FiO_2$ and PEEP to achieve a target value for the oxygen supply of the patient, the first supply control loop being repeated in temporal intervals having a first duration, and
a second supply control loop programmed, in order to increase merely the oxygen concentration in the $FiO_2$ until a renewed setting of $FiO_2$ and PEEP by way of the first supply control loop, as soon as the at least one representative reading for a success of the oxygen supply falls below a certain limit value, the second supply control loop operating between the optimizations controlled by the first supply control loop and being repeated in temporal intervals having a second duration shorter than the first duration.

18. The device according to claim 17, wherein the ventilator includes:
a device for regulation of settings of the ventilator, a sensor for checking the success of the oxygen supply, and a computer with input possibilities for haemodynamic stability of the patient, for an input of a patient parameter, as well as a strategic goal,
wherein said computer being programmed in order to:
automatically compute the PEEP and the $FiO_2$ on account of sensor values and input values, and
to regulate the settings of the ventilator accordingly.

19. The device according to claim 17, wherein the second supply control loop has a shorter temporal interval than the first supply control loop.

20. A method for regulating PEEP- and $FiO_2$-settings of a ventilator for achieving an arterial oxygen partial pressure in blood of a patient mechanically ventilated with the ventilator, the method comprising:
measuring at least one representative reading which is representative of a success of an oxygen supply continuously or at intervals,
optimizing values of PEEP and $FiO_2$ in temporal intervals with a first control loop having a first algorithm to compute a predefined, necessary supply intensity based on the at least one representative reading and a current supply intensity and a second algorithm to evaluate individual values for the PEEP and the $FiO_2$ on account of a necessary supply intensity determined on account of a current representative reading and the current supply intensity and further in temporal intervals having a first duration and activating a ventilator accordingly, and
increasing therebetween, in temporal intervals having a second duration shorter than the first duration the $FiO_2$ with a second control loop on account of a current representative reading.

21. The method according to claim 20, further comprising continuously measuring at least one reading, wherein the at least one reading is representative of the oxygen saturation of the blood.

22. The method according to claim 20, further comprising taking into account a patient parameter, which characterizes a lung condition, in the first algorithm.

23. The method according to claim 20, wherein the first algorithm assigns a representative reading and the current supply intensity in each case to one of three regions, said regions being defined by two characteristic lines distanced to one another, which in each case determine for a given supply intensity a minimal and maximal representative value, and between them define a normal region for the representative value.

24. The method according to claim 23, further comprising forming the first algorithm on a basis of different characteristic line courses according to a patient parameter and strategic goal.

25. The method according to claim 20, further comprising taking into account, in the second algorithm, a haemodynamics input value which characterizes a haemodynamic stability of a patient.

26. The method according to claim 20, wherein the second algorithm determines current values for the PEEP and the $FiO_2$ on account of a diagrammatically representable function that assigns a value for the PEEP to a value for the $FiO_2$.

27. The method according to claim 26, wherein the second algorithm uses different functions depending on a current haemodynamics input value, on a reading indicating haemodynamics of the patient, and on a current patient parameter.

28. The method according to claim 27, wherein, with unstable haemodynamics, an applied function assigns the $FiO_2$ and the PEEP to one another independently of whether the supply intensity is increased or reduced.

29. The method according to claim 27, wherein, with stable haemodynamics, an applied function forms a loop and therefore assigns the $FiO_2$ and the PEEP to one another depending on whether the supply intensity is increased or reduced.

30. The method according to claim 26, further comprising modifying at least one diagrammatically representable function and a newly configured function forming a basis of the second algorithm.

31. The method according to claim 20 further comprising carrying out a recruitment maneuver before a PEEP-increase.

32. A method for regulating settings of a ventilator, comprising:
setting a target frequency and an inspiration pressure with a first ventilation control loop, in order to fulfill target values for an arterial $CO_2$-partial-pressure in a patient's blood and for a ventilation intensity, in accordance with a patient,
reducing a target value for the arterial $CO_2$-partial-pressure by way of a second ventilation control loop, in a temporally limited manner, and increasing a target value for the ventilation intensity, when a measured total respiratory frequency exceeds a computed target frequency by a certain value,
setting an oxygen concentration of respiratory gas $FiO_2$ and end-expiratory pressure (PEEP) with a first $O_2$-supply control loop to control optimizations for values for PEEP and $FiO_2$, in order to fulfill target values for a supply intensity and an oxygen concentration in the patient's blood, in accordance with the patient, the first $O_2$-supply control loop comprising a first algorithm to compute a necessary supply intensity based on at least one representative reading and a current supply intensity and a second algorithm to evaluate individual values for the PEEP and the $FiO_2$ based on a necessary supply intensity determined by a current representative reading, the first $O_2$-supply control loop being repeated in temporal intervals having a first duration, and increasing the oxygen concentration in the respiratory gas ($FiO_2$) by way of a second $O_2$-supply control loop until a renewed setting of the $FiO_2$ and the PEEP by way of the first $O_2$ supply control loop, as soon as a representative reading for the oxygen concentration in the patient's blood falls below a certain limit value, the second $O_2$-supply control loop operating between the optimizations controlled by the first $O_2$-supply control loop and being repeated in temporal intervals having a second duration shorter than the first duration.

33. The method according to claim 32, wherein the second $O_2$-supply control loop is repeated in shorter temporal intervals than the first $O_2$-supply control loop.

34. A device for regulating settings of a ventilator for achieving an adapted mechanical ventilation of a patient, comprising:
at least one sensor for continuous measurement or for the measurement in temporal intervals of at least of one reading representative of the success of the O2-supply, and/or at least one sensor for the continuous measurement or measurement in temporal intervals of at least one reading representative of successful ventilation, a programmed computer, provided with at least one first electronic control loop functioning in a long-term manner, specifically a control loop in order to control optimizations for PEEP and FiO2, and/or a control loop in order to control optimizations for Pinsp and RRIMV on account of the representative reading and a predefined necessary ventilation intensity,
the at least one first electronic control loop comprising a first algorithm to compute a necessary supply intensity based on a representative reading and a current supply intensity, and a second algorithm to evaluate individual values for the PEEP and the FiO2 based on a necessary supply intensity determined by a current representative reading and said computer being programmed in a manner such that the ventilator is activated according to the current optimization, the first electronic control loop being repeated in temporal intervals having a first duration, and
equipped with at least one second electronic control loop functioning in a short-term manner, specifically a control loop, in order between the optimizations by way of the first control loop to increase the FiO2 on account of the current representative value, and/or a control loop, in order between the optimizations by way of the first electronic control loop to increase the ventilation on account of the current representative value, the second electronic control loop being repeated in temporal intervals having a second duration shorter than the first duration;
wherein the first electronic control loop assigns a representative reading to one of three regions which are defined by a characteristic line pair, each characteristic line of the characteristic line pair being defined by oxygen supply intensity on one axis and a representative value of oxygen partial pressure in blood on another axis, and only carries out a change of the parameters FiO2 and/or PEEP when a reading lies outside a middle normal region, wherein the characteristic line pair has a first characteristic line which assigns different minimal representative values of oxygen partial pressure in blood to different values of oxygen supply intensity, and a second characteristic line which assigns in different maximal representative values of oxygen partial pressure in blood to different values of oxygen supply intensity, said first and second characteristic lines being distanced from one another and between them defining the middle normal region for a representative value, and the second electronic control loop assigns the representative reading to one of two regions which are defined by a single characteristic line, and only carries out a change of the FiO2 when the reading lies below the single characteristic line, wherein the single characteristic line assigns different maximal representative values of oxygen partial pressure in blood to different values of oxygen supply intensity, and wherein the single characteristic line used in the second electronic control loop lies below the first characteristic line of the characteristic line pair used in the first electronic control loop, and the middle normal region which is used with the first electronic control loop falls completely within a normal region present above the single characteristic line with the second electronic control loop.

35. The device according to claim 34, further comprising an oxygen sensor for checking oxygen supply of the patient that includes oxygen saturation in the blood of the patient, and a $CO_2$-sensor, for checking the ventilation, that includes checking for an arterial $CO_2$-partial-pressure of the patient.

* * * * *